United States Patent
Burbank et al.

(10) Patent No.: US 10,959,753 B2
(45) Date of Patent: Mar. 30, 2021

(54) CANULA FIXATION DEVICES, SYSTEMS, AND RELATED METHODS

(71) Applicant: INTUITIVE SURGICAL OPERATIONS, INC., Sunnyvale, CA (US)

(72) Inventors: William A. Burbank, Sandy Hook, CT (US); Douglas S. Langley, Milford, CT (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 387 days.

(21) Appl. No.: 15/576,872

(22) PCT Filed: May 27, 2016

(86) PCT No.: PCT/US2016/034612
§ 371 (c)(1),
(2) Date: Nov. 27, 2017

(87) PCT Pub. No.: WO2016/196276
PCT Pub. Date: Dec. 8, 2016

(65) Prior Publication Data
US 2018/0168684 A1    Jun. 21, 2018

Related U.S. Application Data

(60) Provisional application No. 62/168,155, filed on May 29, 2015.

(51) Int. Cl.
*A61B 17/34*    (2006.01)
*A61M 25/02*    (2006.01)
*A61B 17/02*    (2006.01)

(52) U.S. Cl.
CPC ...... *A61B 17/3423* (2013.01); *A61B 17/0218* (2013.01); *A61B 17/3421* (2013.01); *A61M 25/02* (2013.01); *A61B 2017/347* (2013.01); *A61B 2017/3484* (2013.01); *A61M 2025/024* (2013.01); *A61M 2025/0233* (2013.01)

(58) Field of Classification Search
CPC ............ A61B 17/3421; A61B 17/3423; A61B 17/0218
USPC ......................................................... 600/204
See application file for complete search history.

(56) References Cited

U.S. PATENT DOCUMENTS 5,380,302 A    1/1995    Orth
5,556,411 A    9/1996    Taoda et al.
(Continued)

FOREIGN PATENT DOCUMENTS

WO    WO-9425095 A1    11/1994

OTHER PUBLICATIONS

Extended European Search Report for Application No. EP16804110.1, dated Dec. 3, 2018, 6 pages.
(Continued)

*Primary Examiner* — Si Ming Ku
(74) *Attorney, Agent, or Firm* — Jones Robb, PLLC

(57) ABSTRACT

A cannula fixation device for insertion at a surgical incision includes a sleeve having a passage configured to receive a cannula, and a clamp configured to rotatably couple the cannula to the sleeve and to maintain an axial position of the cannula relative to the sleeve.

17 Claims, 9 Drawing Sheets

(56) References Cited

U.S. PATENT DOCUMENTS

| | | |
|---|---|---|
| 8,162,893 B2* | 4/2012 | Okihisa .............. A61B 17/3421 604/165.01 |
| 2003/0040753 A1 | 2/2003 | Daum et al. |
| 2010/0010449 A1 | 1/2010 | Leibowitz et al. |
| 2014/0066953 A1 | 3/2014 | Keating et al. |

OTHER PUBLICATIONS

International Search Report and Written Opinion for Application No. PCT/US16/34612, dated Sep. 9, 2016, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

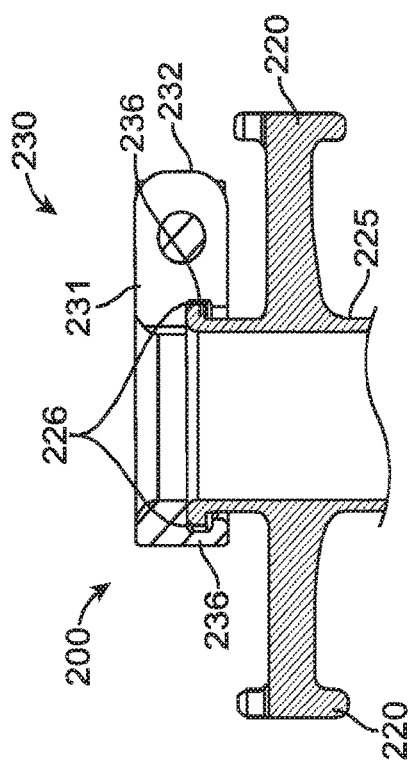
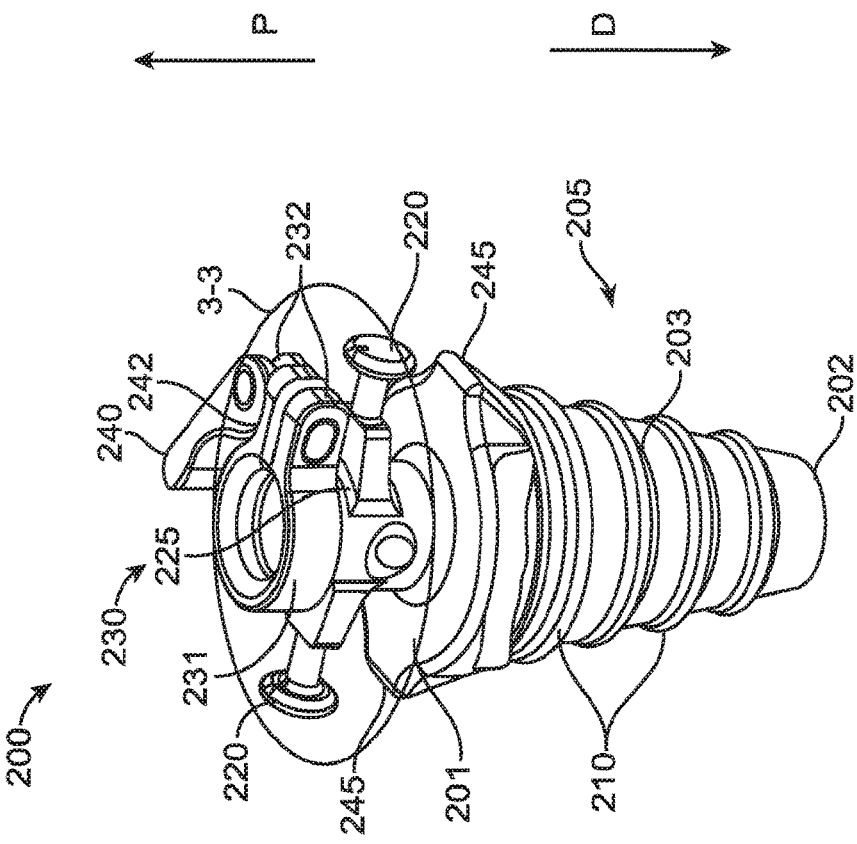

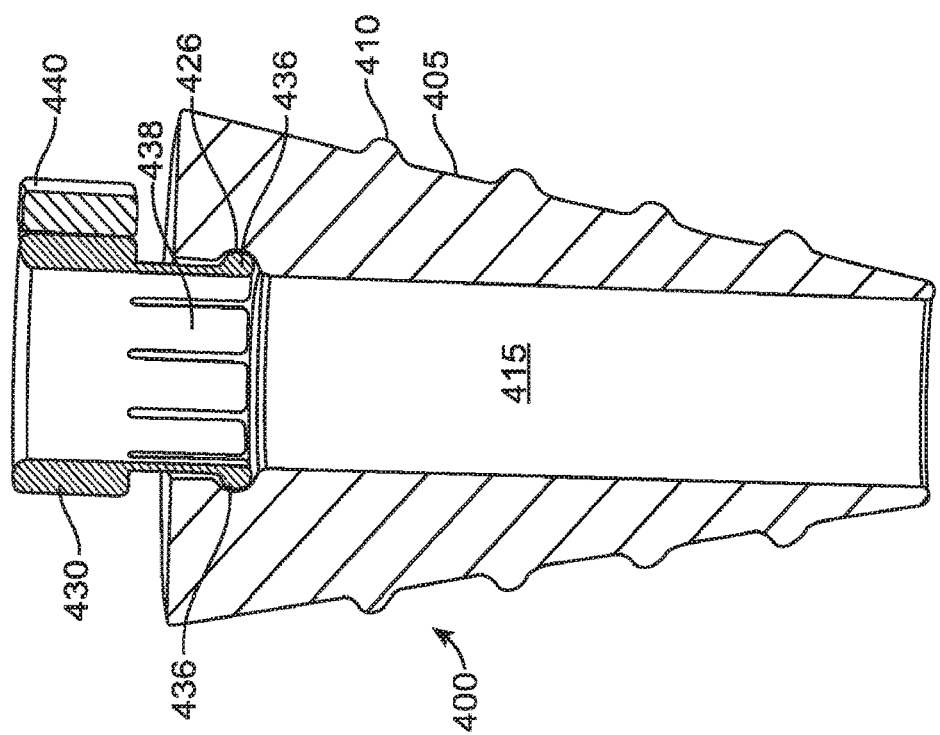
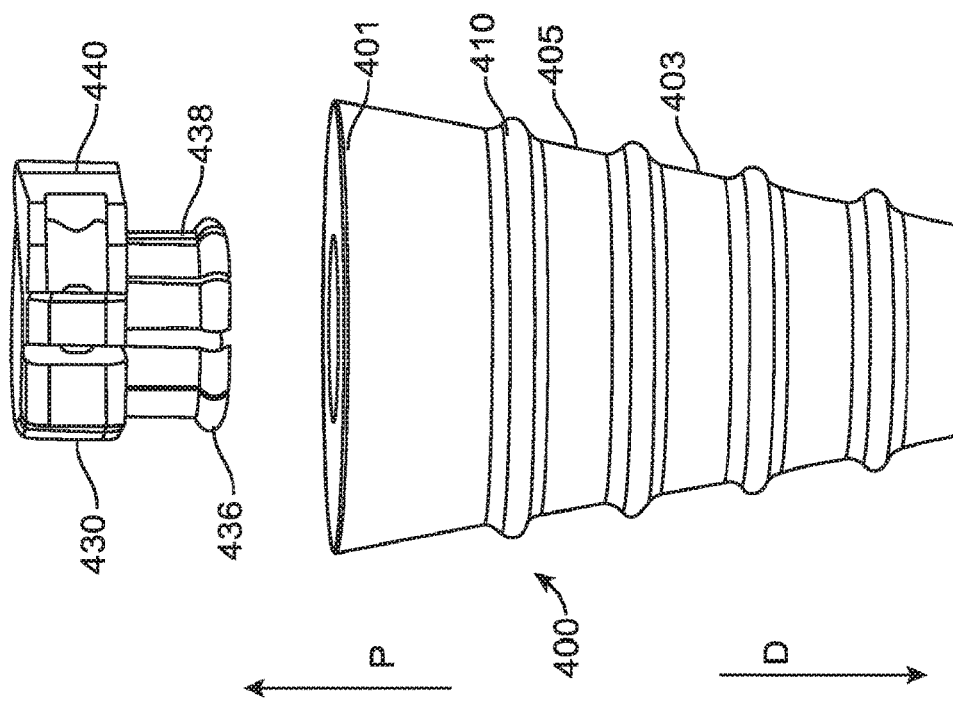

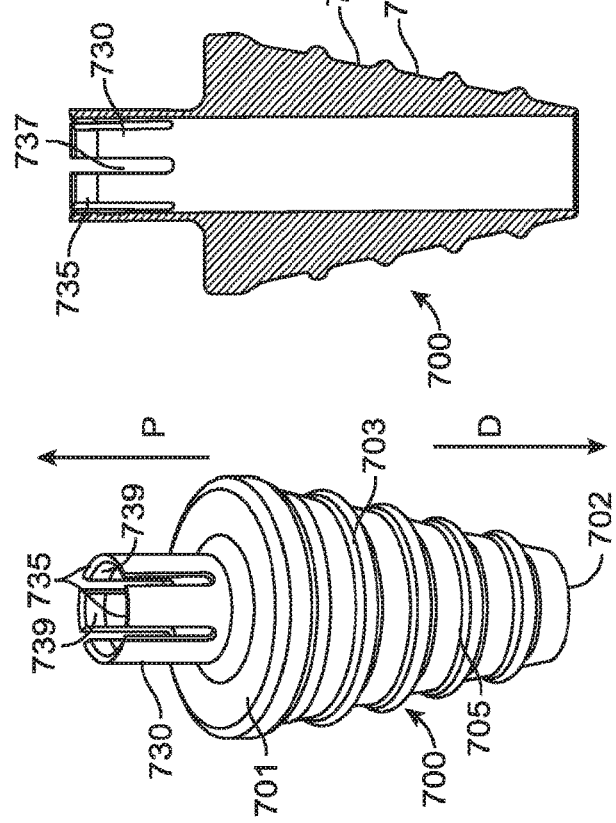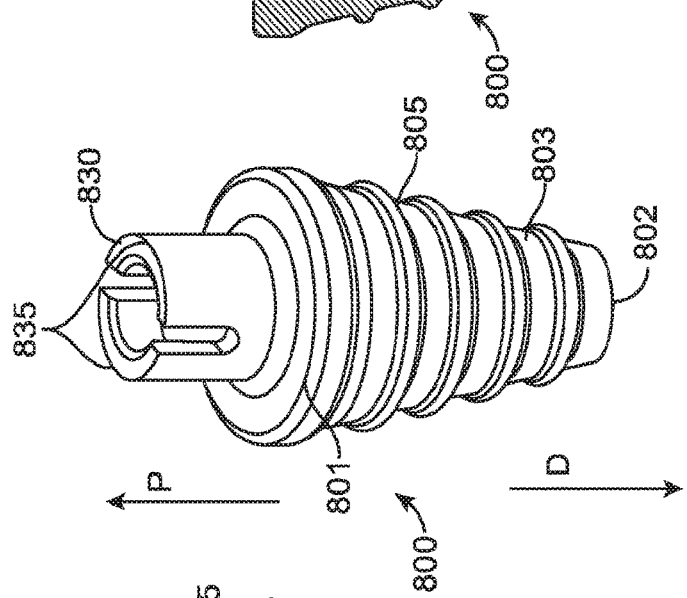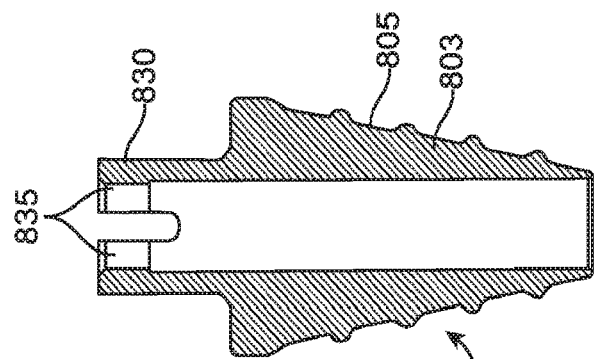
FIG. 14
FIG. 15
FIG. 16
FIG. 17

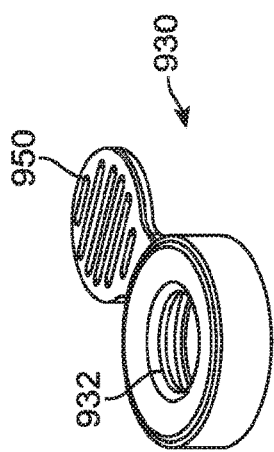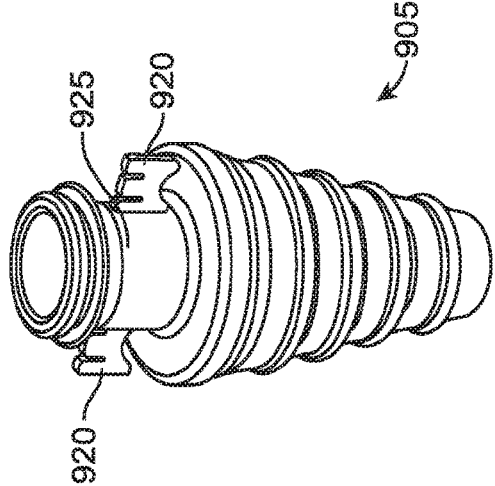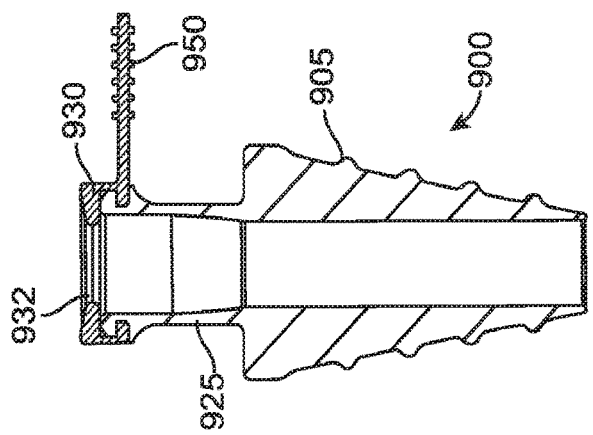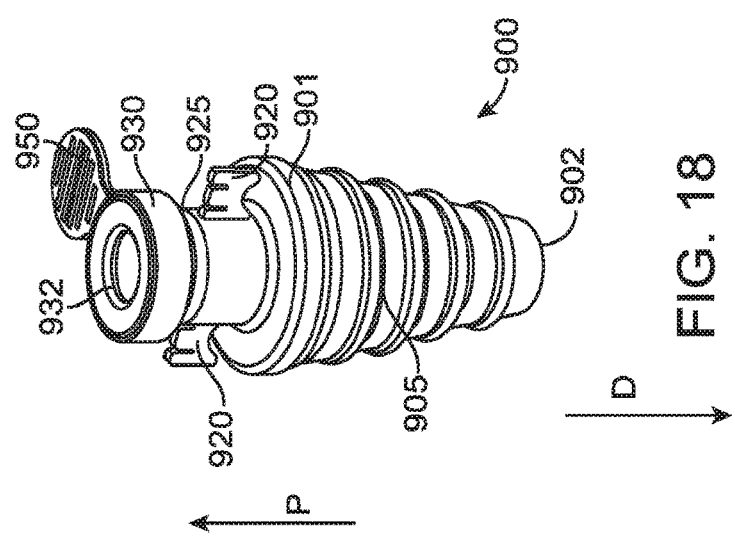

CANULA FIXATION DEVICES, SYSTEMS, AND RELATED METHODS

RELATED APPLICATIONS

This patent application is a national stage under 35 U.S.C. § 371 (c) of International Application No. PCT/US2016/034612, filed May 27, 2016, which claims priority to and the benefit of the filing date of U.S. Provisional Patent Application 62/168,155 (now expired), entitled "CANNULA FIXATION DEVICES, SYSTEMS, AND RELATED METHODS" filed May 29, 2015, each of which is incorporated by reference herein in its entirety.

TECHNICAL FIELD

Aspects of the present disclosure relate to fixation devices for surgical cannulas, and related systems and methods.

INTRODUCTION

Various surgical procedures rely on cannulas inserted through an incision in a patient to provide access to a surgical or diagnostic site. In an open access laparoscopic surgical procedure, sometimes referred to as a "Hasson" procedure after the name of the individual who developed the technique, the cannula is inserted through a frusto-conical shaped fixation sleeve that is used to both hold the cannula in place and also to provide a seal between the cannula and the body wall of the patient at the incision site. In this way, insufflation gas used in the surgical procedure can be prevented from leaking through the incision around the cannula and fixation sleeve (e.g., allowing surgical-induced pneumoperitoneum to be maintained) since the initial incision is generally larger than the cannula outer diameter. The fixation sleeve (sometimes referred to as a Hasson cone) also generally locks on to the outer surface of the cannula to fix and stabilize the cannula's inserted position during the introduction of surgical tools through the cannula during the surgical procedure. Relative movement of the cannula relative to the sleeve is prevented in this locked configuration. To prevent movement of the sleeve, and thus the cannula, relative to the body wall of the patient, the sleeve is typically sutured to the patient's body wall around the incision.

Such cannula fixation sleeves are used both in manual minimally invasive surgical procedures, such as, for example, laparoscopic procedures, and in computer-assisted teleoperated surgical techniques. However, as will be set forth in further detail below, conventional cannula fixation sleeves are in need of further improvement to enhance their ability to maintain a seal and adequately hold the cannula in place during various movements of the cannula, while continuing to maintain the robustness and relative simplicity in the structure and use of such devices.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a cannula fixation device for insertion at a surgical incision includes a sleeve having a passage configured to receive a cannula, and a clamp configured to rotatably couple the cannula to the sleeve and to maintain an axial position of the cannula relative to the sleeve.

In accordance with at least one exemplary embodiment, method of holding a cannula in position through an insertion site during a surgical procedure include holding the cannula in a fixed axial position relative to a sleeve positioned at the insertion site, the sleeve sealing against a body wall of the insertion site to prevent leakage of insufflation gas through the insertion site, and permitting rotational movement of the cannula relative to the sleeve while maintaining the fixed axial position of the cannula during the surgical procedure.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims. The claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

FIG. 2 is a perspective view of a cannula fixation device according to an exemplary embodiment.

FIG. 3 is partial cross-sectional view of portion 3-3 of the cannula fixation device of FIG. 2.

FIG. 7 is a perspective view of yet another exemplary embodiment of a cannula fixation device in accordance with the present disclosure, showing a clamp of the cannula fixation device uncoupled from a fixation sleeve of the device.

FIG. 8 is a longitudinal sectional view of the cannula fixation device of FIG. 7, showing the clamp coupled to the fixation sleeve.

FIG. 14 is a perspective view of another exemplary embodiment of a cannula fixation device in accordance with the present disclosure.

FIG. 15 is a longitudinal sectional view of the cannula fixation device of FIG. 14.

FIG. 16 is a perspective view of another exemplary embodiment of a cannula fixation device in accordance with the present disclosure.

FIG. 17 is a longitudinal sectional view of the cannula fixation device of FIG. 16.

FIG. 18 is a perspective view of yet another exemplary embodiment of a cannula fixation device in accordance with the present disclosure.

FIG. 19 is a longitudinal sectional view of the cannula fixation device of FIG. 18.

FIG. 20 is a perspective, isolated view of the clamp of the cannula fixation device of FIG. 18.

FIG. 21 is a perspective, isolated view of the fixation sleeve of the cannula fixation device of FIG. 18.

DETAILED DESCRIPTION

Figure 1:
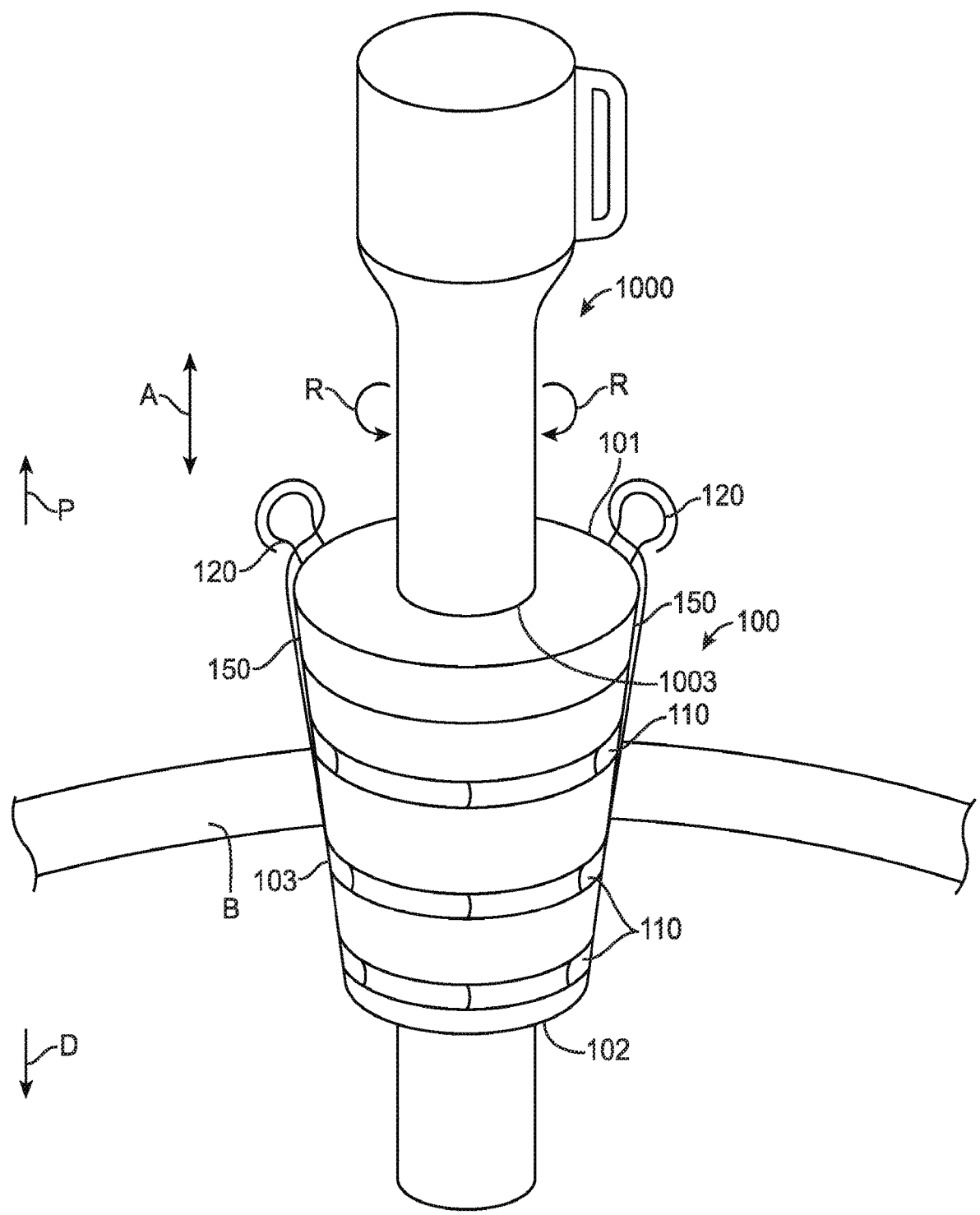
FIG. 1 is a perspective view of a cannula and cannula fixation device inserted in position in a body wall of a patient in accordance with an exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

As discussed above, cannula fixation sleeves are used in minimally invasive surgical procedures, whether performed as manual laparoscopic procedures or as computer-assisted teleoperated surgical procedures, for example using computer-assisted teleoperated surgical systems such as a da Vinci Si® Surgical System, Single Site™ da Vinci® Surgical System, or a da Vinci® Xi™ Surgical System, and other systems commercialized by Intuitive Surgical, Inc. of Sunnyvale, Calif. Various conventional cannula fixation sleeve configurations lock onto the outer diameter of the cannula in a manner that prevents axial and rotational movement of the cannula relative to the sleeve. Axial refers to an orientation along a longitudinal axis between a proximal (away from the surgical site) end and distal (toward the surgical site) end of the cannula or the cannula fixation sleeve. Rotational refers to a rotational direction (clockwise or counterclockwise) around the longitudinal axis.

In some cases, however, rotation of a cannula can occur during a surgical procedure. By way of example, in various computer-assisted teleoperated surgical systems, cannulas mounted to arms of a patient side cart are moved around a remote center of motion during the teleoperation of the surgical instruments during a surgical procedure. The motion of the cannulas in such teleoperated surgical systems is an automated response to the overall motion control schemes used in the teleoperated surgical systems, making some of the movements experienced by the cannula difficult to predict in advance by a surgeon and other surgical personnel. For example, a large cannula pitch motion from a starting pitch/yaw orientation, followed by a large cannula yaw motion, followed by a large pitch motion back to the starting pitch/yaw orientation can result in a cannula roll (rotation around the longitudinal axis of the cannula) at the incision.

Rotational movement of a cannula to which a conventional cannula fixation sleeve is locked in turn can cause rotation of the sleeve with the cannula. Under sufficient amount of rotational force, the sutures holding the fixation sleeve can be compromised, allowing the fixation sleeve to become displaced relative to the body wall, which in turn may lead to failure of the seal between the sleeve and body wall, relative movement (including in an axial direction of the cannula) between the body wall and the cannula and sleeve, and/or trauma at the incision site.

To address these and other issues, various exemplary embodiments in accordance with the present disclosure contemplate a cannula fixation device that can clamp onto the cannula to prevent axial movement between the cannula fixation device and the cannula, while also permitting free rotation of the cannula relative to the portion of the fixation device that forms the seal with the body wall. Such a configuration can permit the cannula to rotate without in turn applying a load on the sutures as a result of such rotation that could compromise the sutures.

Various exemplary embodiments of the present disclosure further contemplate cannula fixation device configurations that permit cleaning fluids to access various internally situated portions of the device so as to ensure such devices can be sufficiently cleaned during flushing and brushing procedures. Such configurations can permit cannula fixation devices to be reused for multiple surgical procedures.

To further permit reuse of cannula fixation devices, exemplary embodiments in accordance with the present disclosure contemplate using materials, such as biomedical grade materials, for the device that render the device autoclavable, such as, for example, biomedical grade metals including, but not limited to, stainless steel, and biomedical grade plastics including, but not limited to a variety of high temperature resins (e.g., PPSU (polyphenylsulfone), PEEK (polyether ether ketone), PSU (polysulfone), PPO (p-phenylene oxide), PTFE (polytetrafluoroethylene), PEI (polyetherimide)). In yet other exemplary embodiments, the cannula fixation device may be designed to be a single-use device and disposable, in which case, it may be made of biomedical grade plastic materials. Fixation devices made of plastic materials also may reduce the weight of the device, thereby potentially reducing the inertia/weight acting on a manipulator arm of the telesurgical patient side cart with which the devices may be used in various exemplary embodiments.

The present disclosure further contemplates various exemplary embodiments that provide cannula fixation devices with features on their outer periphery to help reduce the risk of the fixation devices rolling off surfaces on which they may be placed (e.g., surgical trays, operating room tables, cleaning facility tables, etc.) prior to insertion at the incision site. Cannula fixation devices can be damaged on impact with the floor, and sterilization will be compromised.

Other aspects and features of exemplary embodiments of cannula fixation devices in accordance with the present disclosure will be discussed below.

With reference to FIG. 1, a schematic representation of a cannula and cannula fixation device, inserted in position into a body wall B of a patient at a surgical incision site, is depicted. As shown, the fixation device 100 has a generally frusto-conical shape with a tapered outer surface 103 which optionally can include various ribs 110, threads, knurling, or other similar surface features to assist with creating an interference with the body wall B of a patient in a position of the fixation device 100 inserted into an incision opening in the body wall B. The outer surface 103 tapers from the proximal end 101 to the distal end 102. In the orientation of the exemplary embodiments of the figures, the proximal direction of the devices is labeled P and the distal direction is labeled D. The tapered outer (lateral) surface profile assists in the ability to insert the fixation device around a cannula to various depths to accommodate various sized incision openings, thereby ensuring a sufficient seal about the inserted fixation device to prevent insufflation gas leakage and relative movement of the fixation device relative to the body wall. The surface features 110 are optional, and various exemplary embodiments can include fixation devices without such surface features or have surface features of other configurations and arrangements.

The fixation device 100 further includes a central internal passage extending between openings at opposite ends 101, 102 of the device 100. The central internal passage is sized to receive a cannula 1000 so as to permit the cannula to be inserted through the incision site and into the body cavity in which a surgical procedure is to be performed. In accordance with various exemplary embodiments, in the inserted position of the cannula and fixation device 100 in the body wall, the fixation device 100 is held in place via one or more sutures 150, for example, in a purse-string arrangement, around the opening of the incision. Although two sutures 150 are illustrated in FIG. 1, those having ordinary skill in the art will appreciate that a number of sutures may be used to sufficiently attach and seal the fixation device to the body wall. The fixation device can further include suture stay features 120 to which the sutures 150 may be tied off and accessed as desired to close the incision after removal of the cannula and fixation device. The suture stay features 120 can have numerous arrangements and configurations, as will be demonstrated with the description of various exemplary embodiments described further below.

The fixation device 100 is configured to be releasably securable to the cannula 1000. In the secured state, the fixation device 100 clamps to the outer surface 1003 of the cannula 1000 with a force sufficient to prevent movement of the cannula 1000 in axial directions A. The fixation device 100 also is configured to be placed in a released state in which the fixation device 100 permits movement of the cannula 1000 relative to the fixation device 100 in axial directions A. The ability to relatively easily secure the cannula fixation device and the cannula to each other to maintain the axial position of the cannula, while also permitting the cannula to be relatively easily released from the fixation device, can assist surgical personnel in both positioning the cannula to ready it for a surgical procedure and also removing and/or reorienting the cannula (e.g., in pitch, yaw and/or roll) as needed.

The fixation device 100 is further configured in both the secured states and the released states to permit rotation of the cannula 1000 in directions R relative to the fixation device 100. Permitting the relative rotation of the cannula 1000 with respect to the fixation device 100, even in the releasably secured state of the fixation device 100 to the cannula 1000 allows the cannula 1000 to rotate around the cannula's longitudinal axis relative to the fixation device 100. Accordingly, consequent rotational motion of the fixation device 100 can be prevented, which motion could result in forces acting on, and potentially compromising, the sutures 150, and/or result in tissue trauma at the incision. Thus, the fixation device 100 allows for rotational movement of the cannula 100 around the cannula's longitudinal axis that may occur during a surgical procedure, while maintaining the axial position and insertion depth of the cannula 1000 as cannula orientation changes. In addition, the axial and rotational position of the outer surface 103 of fixation device 100 relative to the body wall is maintained.

Cannula fixation devices in accordance with the present disclosure can include a variety of configurations that permit them to be releasably secured to cannulas and also to permit the relative rotation of the cannulas relative to the fixation devices, including while the fixation device is in a secured state, as described above.

One exemplary embodiment of a cannula fixation device in accordance with the present disclosure is illustrated in FIGS. 2-5. The exemplary embodiment of a cannula fixation device 200 depicted in FIGS. 2-5 includes a sleeve 205 and a clamp 230. The sleeve 205 has a generally frusto-conical shape with an outer surface 203 that tapers from a proximal end 201 to a distal end 202 of the sleeve 205. As mentioned above, the outer surface 203 of the sleeve 205 may optionally include surface features 210, such as, for example, ribs, threading, knurling, configured to assist with creating an interference fit with the body wall of a patient to help seal the fixation device 200 in body wall. In particular, such surface features can be beneficial due to the different layers of the body wall and uneven cuts going through those layers. Alternatively, the outer surface of the sleeve 205 may be relatively smooth and free of such surface features. As further described above, the sleeve 205 includes a central passage 215 (shown best in the views of FIGS. 4 and 5) configured to receive a cannula (not shown).

As noted above, the fixation device 200 further includes a clamp 230 rotatably coupled to the fixation sleeve 205. More specifically, the fixation sleeve 205 includes a neck portion 225 that extends axially from the proximal end 201 of the sleeve 205 into which a cannula (not shown) is inserted during introduction into the sleeve 205 and to the remote surgical site. The clamp 230 is rotatably coupled to a proximal end of the neck 225. As shown best in FIG. 3, the rotatable coupling of the clamp 230 to the neck 225 is accomplished by a lip 226 that extends around the outer periphery of the end of the neck 225. The lip 226 is received in a groove 236 in an inner peripheral surface of the clamp 230. The fit between the lip 226 and groove 236 prevents removal of the clamp 230 from the neck 225 and limits the extent of axial motion of the clamp 230 and sleeve 205 relative to one another. However, clearances between the lip 226 and the surfaces of the groove 236 are sufficient to allow for relatively unhindered rotation of the clamp 230 and sleeve 205 relative to one another in either the clockwise or counterclockwise directions. In addition, the clearances are sufficient to permit cleaning of the fixation device 200, by allowing access between those parts by flushing fluids and in some cases cleaning brushes and the like. In various exemplary embodiments, the radial clearance between the recessed surfaces defining the groove 236 and the lip 226 can range from about 0.0015 in. to 0.025 in. In various exemplary embodiments, the clamp 230 is positioned around the neck 225 during manufacture of the fixation device 200 and is not releasable from the neck by a user.

Figure 5:
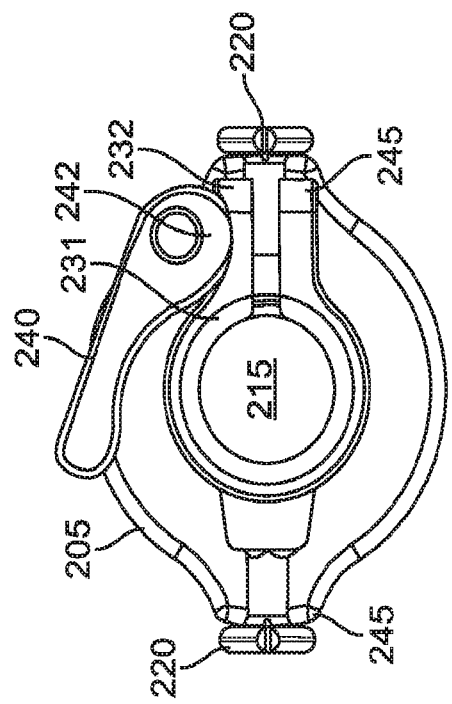
FIG. 5 is an axial end view of the cannula fixation device of FIG. 2, observed from a direction facing the clamp and illustrating the fixation device in a secured state.
Figure 4:
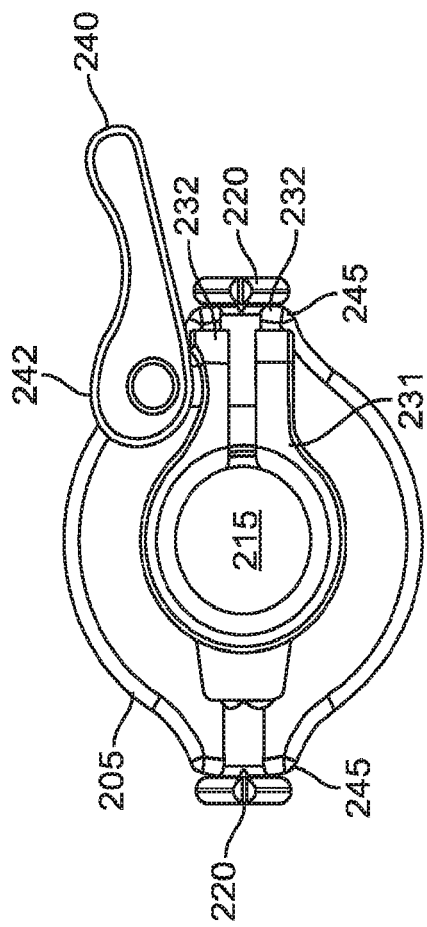
FIG. 4 is an axial end view of the cannula fixation device of FIG. 2, observed from a direction facing the clamp and illustrating the fixation device in a released state.

The clamp 230 includes C-clamp member 231 having extension ends 232 to which a lever 240 is coupled. The lever 240 has a cam surface 242 that moves into and out of engagement with one of the extensions 232 depending on the position of the lever 250. The movement of the lever 240, and consequent movement of the cam surface 232 into and out of engagement with one of the extensions 232 of the C-clamp member 231, moves the clamp 230 between a relatively more open and a relatively more closed configuration so as to be able to clamp onto and unclamp from an outer surface of a cannula). For example, FIGS. 4 and 5 depict the clamp 230 and lever 240 in the open configuration and the closed configuration, respectively. In FIG. 4, the lever 240 is pivoted such that the cam surface 242 is not in contact with the extension 232 of the C-clamp member 230. Thus, in FIG. 4, the clamp 230 is relatively more open. In FIG. 5, the lever 240 is pivoted to a position such that the cam surface 242 contacts and presses against the one of the extensions 232. As a result of the cam surface 242 engagement and the coupling of the lever 240 to the extensions 232, the extensions 232 are brought toward each other to place the clamp 230 in a relatively more closed position.

As would be appreciated by one of ordinary skill in the art, the clamp 230, therefore, can be releasably clamped and secured in an axial fixed position onto a cannula. Accordingly, given a cannula of appropriate dimensions, in the relatively open position of the clamp 230 and lever 240 (corresponding to the released, unclamped state of the fixation device), as depicted in FIG. 4, the clamp 230 and cannula can move axially relative to each other, and in the relatively closed position of the clamp 230 and lever 240 (corresponding to a secured, clamped state of the fixation device) as depicted in FIG. 5, the clamp 230 can engage and be secured to the cannula to prevent axial movement of the cannula. Regardless of whether the clamp 230 is engaged and secured to the cannula as in the state of the clamp 230 in FIG. 5 or is released from the cannula in the relatively open position as in the state the clamp 230 in FIG. 4, the clamp will permit the cannula to rotate relative to the fixation sleeve 205. In the relatively closed configuration of the clamp 230 in FIG. 5, the clamp 230 can be secured to the cannula so as to prevent axial movement of the cannula relative to the fixation device 200, while permitting rotation of the cannula relative to the fixation sleeve 205 and body wall of the patient in an inserted position of the fixation device 200 and cannula.

To provide a smooth bearing surface as well as flexibility and give when clamping against the outer surface of a cannula, at least an inner surface of the clamp 230 can be made of relatively high strength, engineering thermoplastic materials, although such choice of material is considered to be nonlimiting and exemplary only. In particular, in accordance with various exemplary embodiments, as noted above, it may be desirable to make the fixation device out of an autoclavable and biomedical grade metal to promote reuse of the device. Moreover, in some exemplary embodiments, at least the fixation sleeve portion of the device may be made of a conductive material sufficient to provide an electrical path to ground, which may be useful to aid in providing capacitive coupling when using electrosurgical instruments in the cannula.

As shown with reference to FIGS. 2 and 3, the exemplary embodiment of the fixation device 200 also can include suture stays 220 extending laterally (e.g., radially) outward from the neck portion 225. Although the exemplary embodiment of FIGS. 2-4 illustrate two suture stays 220 disposed generally diametrically opposite to each other and extending in opposite directions, other numbers, including a single suture stay, and arrangements of suture stays are considered to be within the scope of the present disclosure.

Also, in accordance with various exemplary embodiments, cannula fixation devices can be provided with anti-roll features to assist in preventing the fixation devices, due to their rounded outer surface profiles, from rolling off surfaces, such as surgical trays and the like. As illustrated in the exemplary embodiment of the cannula fixation device 200 in FIGS. 2, 4, and 5, for instance, the proximal end 201 of the fixation sleeve 205 may include one or more (with two being depicted) anti-roll peripheral surface features, for example, in the form of bosses 245. Such anti-roll bosses 245 can be helpful to limit rolling of the fixation device 200, in particular when the suture stays 220 do not extend significantly outside of the imaginary outer envelope defined by extending the conical outer surface upward past the neck portion 225 of the fixation device 200. Persons having ordinary skill in the art would appreciate that the number, configuration, and arrangement of the anti-roll surface features can vary from those shown in the exemplary embodiment of FIGS. 2, 4, and 5.

Figure 6:
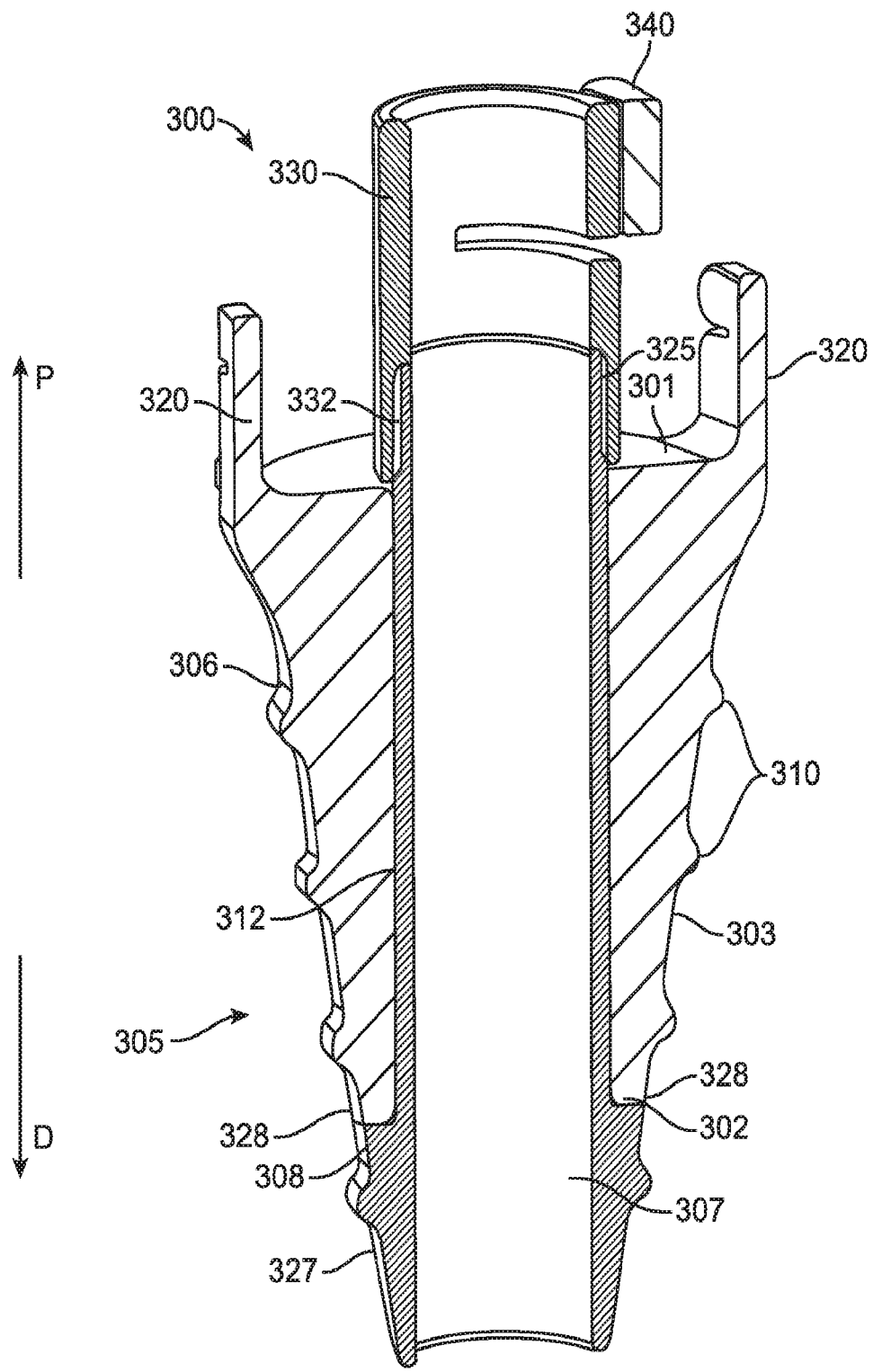
FIG. 6 is a longitudinal perspective sectional view of another exemplary embodiment of a cannula fixation device in accordance with the present disclosure.

FIG. 6 is a longitudinal sectional view of another exemplary embodiment of a cannula fixation device in accordance with the present disclosure, with proximal and distal directions of the device being illustrated by arrows labeled P and D, respectively. The cannula fixation device 300 of FIG. 6 is a multi-component structure that permits the fixation sleeve 305 to be de-coupled from the clamp 330. The fixation sleeve 305 includes two parts, an outer main body part 306, which has a frusto-conical shape and is tapered from a proximal end 301 to a distal end 302, and an inner tube 307 that extends centrally through the outer main body part 306 to form the central passage of the fixation device 300 through which the cannula is inserted. The proximal end of the inner tube 307 forms a neck 325 of the fixation device 300 to which the clamp 330 can be coupled, as will be explained in further detail below. The opposite, distal end of the inner tube includes a tapered collar 327 that provides a shoulder 328 for the distal end 302 of the outer main body part 306 to rest on. In the position of the inner tube 307 inserted in the outer main body part 306 with the lower end of the outer main body part 306 resting on the shoulder 328, the tapered outer surface of the collar 327 follows the taper of the outer surface 303 outer main body part 306 to complete the frusto-conical shape of the fixation sleeve 305.

The outer main body part 306 further includes suture stays 320 that extend upwardly from a proximal end 301 of the outer main body part 306. As described above with respect to the exemplary embodiment of FIGS. 2-5, the number and arrangement of the suture stays 320 depicted in FIG. 6 is exemplary and non-limiting, and those of ordinary skill in the art would appreciate various other configurations and arrangements of suture stays can be provided without departing from the scope of the present disclosure. As illustrated in the exemplary embodiment of FIG. 6 and also as described above with respect to the exemplary embodiment of FIGS. 2-5, the outer surface 303 of the fixation device 300 may optionally include surface features, with a series of ribs 310 being depicted, to assist in maintaining a position and interference of the fixation device 300 and body wall. As further described with reference to the exemplary fixation device 200, other configurations and arrangements of surface features on the outer surface 303 of the outer main body part 305 also can be used in the embodiment of FIG. 6, or the outer surface 303 can be smooth and free of such surface features.

Clamp 330 can have a similar configuration as the clamp 230 described above with reference to the exemplary embodiment of FIGS. 2-5, including a C-shaped member with extensions and a cam and lever mechanism to move the clamp between relatively more open and more closed configurations for releasably securing the clamp 330 to a cannula. Accordingly, details regarding those aspects of the clamp 330 are not described here. However, the engagement of the clamp 330 with the fixation sleeve 305 differs from that in the embodiment of FIGS. 2-5. In particular, rather than the lip/groove coupling of the clamp 230 and the neck 225 in the exemplary embodiment of FIGS. 2-5, the exemplary embodiment of FIG. 6 utilizes a threaded engagement 332 between the clamp 330 and the neck 325. The fixation device components are configured such that when the clamp 330 and neck 325 are fully engaged (i.e., the clamp is threaded onto the neck 325 in a direction toward the outer main body part 306), the outer main body part 306 is captured and held in a generally fixed axial position between the collar 327 of the inner tube 307 and the clamp 330. In particular, the distal end of the clamp 330 is adjacent to the proximal end 301 of the outer main body part 306 while the shoulder 328 is adjacent to the distal end 302 of the outer main body part 306. In this captured position, there remains sufficient radial clearance and low friction between the interface 312 of the outer surface of the inner tube 307 and the inner surface of the outer main body part 306 to permit the inner tube 307 and clamp 330 to freely rotate relative to the outer main body part 306. The threaded engagement also allows the clamp 330 to be removed from the neck 325, so as to release the inner tube 307 from the outer main body part 306. In this way, cleaning of the various components of the fixation device 300 may be facilitated. Further, the inner tube and clamp that may be subject to more wear and/or be made of more flexible materials may be able to be disposed of and replaced, while the sleeve 305 is reused and repaired by providing a new tube and/or clamp.

As with the embodiment of FIGS. 2-4, the clamp 330 can be releasably secured to a cannula so as to maintain an axial position of the cannula relative to the fixation device 300. In the secured state of the clamp 330 to the cannula and with the cannula inserted through the inner tube 307 of the fixation device 300, the cannula is able to rotate relative to the outer main body part 306 without transferring the rotational load to the outer main body part 306 and from that part to the sutures holding the fixation device 300 to the body wall of a patient.

In the exemplary embodiment of FIG. 6, various biomedical grade materials can be used to make the different parts, as described above. Moreover, it may be desirable to use materials that have sufficient gall resistance, such as, for example, Nitronic 60 or similar stainless steel alloys, in the threaded area and the bearing surfaces. To reduce the expense of material choice, different materials for the different components may be selected based on considerations of wear and galling due to the uses of the devices, as those of ordinary skill in the art would understand.

Although a threaded engagement of the clamp 330 and inner tube 307 is described above, other engagement mechanisms to removably secure the clamp 330 relative to the inner tube 307 and in a position so as to capture and hold the outer main body part 306 axially also may be used and are contemplated as within the scope of the present disclosure. Suitable alternative engagement mechanisms include, but are not limited to, a bayonet style twist lock mechanism, a set screw, or a slip fit. A press fit between the clamp 330 and the inner tube 307 also may be used, but in such a case, the clamp 330 would not be removable from the inner tube 307.

Another exemplary embodiment of a cannula fixation device in accordance with the present disclosure is illustrated in FIGS. 7 and 8. As with the exemplary embodiment of FIG. 6, the fixation device 400 of FIGS. 7 and 8 includes multiple components configured to be removable from one another. The fixation device 400 includes a frusto-conical shaped fixation sleeve 405 having an outer surface 403 that tapers from the proximal end 401 to the distal end 402. The outer surface 403 has optional ribs 410 or other surface features as described above with respect to various exemplary embodiments and thus not described in further detail here. Further, optional suture stays, as described above, may be provide on the fixation sleeve 405, although not illustrated in FIGS. 7 and 8. The fixation sleeve 405 also includes a central passage 415 that extends between the proximal and distal ends 401, 402 of the sleeve 405. The central passage 5 configured to receive a cannula (not shown in FIGS. 7 and 8) with sufficient clearance and low friction between the cannula and inner surface of the passage 415 so as to permit rotation of the cannula relative to the fixation sleeve 405.

The fixation device 400 further includes a clamp 430 that is configured similarly to the C-clamp member and cam and lever structure described in detail with reference to the exemplary embodiments of FIGS. 2-5. The clamp 430, however, has a different engagement structure for coupling the clamp 430 to the fixation sleeve 405. As depicted in FIGS. 7 and 8, extending axially from the C-clamp member of the clamp 430 are a series of resilient spring fingers 438 slightly biased radially outwardly. At the bottom ends of the spring fingers 438, small convex surface protrusions 436 face radially outward from a radial outer surface of the fingers 438. As shown in FIG. 8, the protrusions 436 are configured to engage in a snap-fit manner with a mating groove 426 provided around an inner upper surface periphery of the passage 415. Prior to insertion of the cannula, with sufficient force in the axial direction away from the fixation sleeve 405, the clamp 430 can be configured to overcome the snap-fit force to pull the clamp 430 out of engagement with the sleeve 405. In an inserted position of the cannula through the clamp 430 and passage 415 in the configuration of FIG. 8, however, the cannula presses slightly outwardly on the fingers 438 to lock the clamp 430 in place axially relative to the fixation sleeve 405. The radial clearance between the finger protrusions 436 and the groove 426 is sufficient, however, to permit rotation of the clamp 430 relative to the sleeve 405. Such relative rotation also is permitted when the clamp 430 is in a secured state to hold the cannula in the configuration of the fixation device depicted in FIG. 8, and likewise there is sufficient radial clearance and low friction between the outer surface of the cannula and the inner surface of the passage 415 to permit relatively unimpeded rotation of the cannula held by the clamp 430 and extending through the fixation sleeve 405. Accordingly, as with other exemplary embodiments, even in a secured state of the fixation device 400 to the cannula to maintain the axial position of the cannula, rotation of the cannula can occur without rotation of the fixation sleeve 405 and consequent forces acting on the sutures holding the fixation device 400 in place to the body wall at the incision. In various exemplary embodiments, radial clearance between the protrusions 436 and the groove 426 can range from 0.0015 in. to 0.025 in.

Further, as with the configuration of the fixation device 300, the fixation device 400 can permit de-coupling of the clamp 430 from the sleeve 405 to facilitate cleaning of the fixation device 400 by providing access to otherwise difficult to reach portions of the device and/or to permit repair and replacement of parts of the device. Moreover, using the lever 440, the clamp 430 can be readily placed in a relatively open position to place the fixation device in a released state permitting the cannula to be removed and/or repositioned axially relative to the fixation device 400. Moreover, the fixation device 400 can be made of the various biomedical grade materials described above, and the various parts may be made of different materials, with material selection for various parts of the fixation device 400 taking into account similar considerations as those described above with respect to the exemplary embodiment of FIG. 6.

Figure 10:
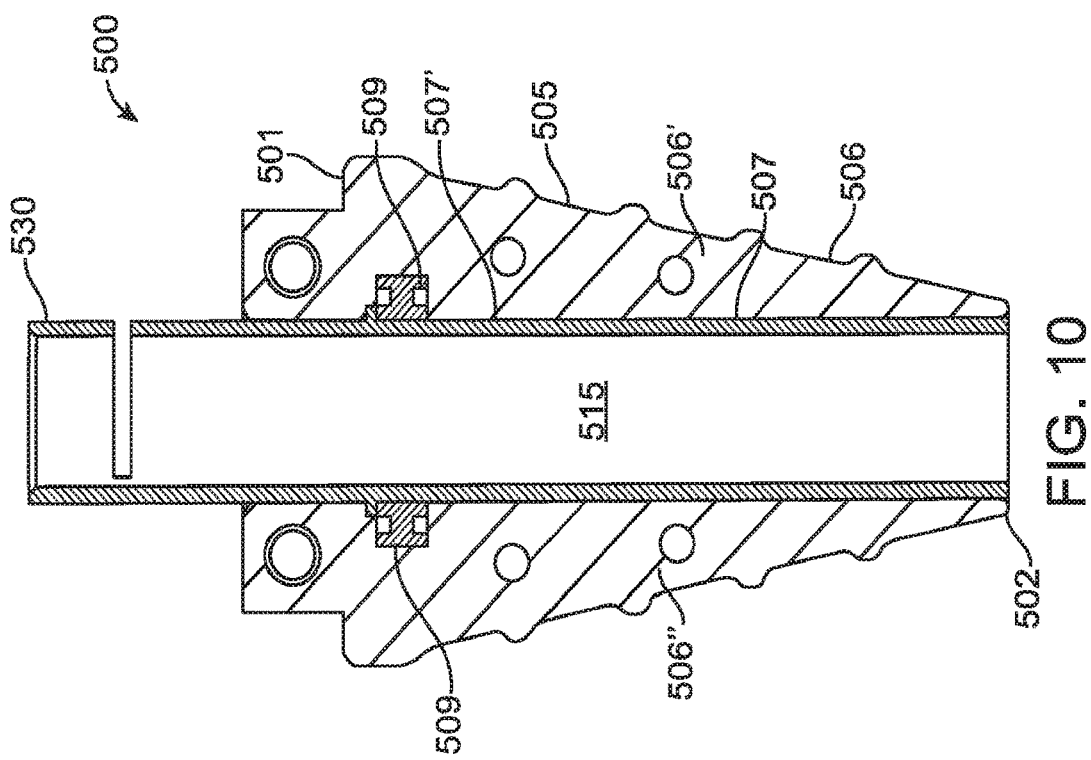
FIG. 10 is a longitudinal sectional view of the cannula fixation device of FIG. 9.
Figure 9:
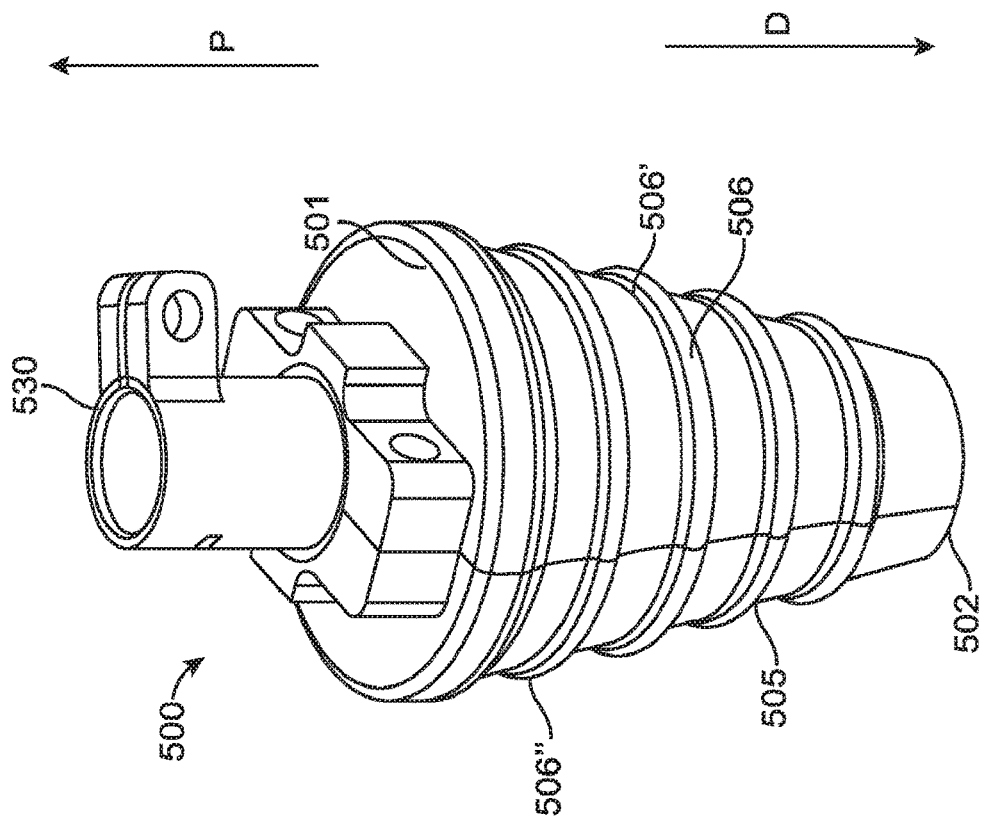
FIG. 9 is a perspective view of yet another exemplary embodiment of a cannula fixation device in accordance with the present disclosure.

Yet another exemplary embodiment of a cannula fixation device in accordance with the present disclosure is shown in FIGS. 9 and 10. In this embodiment, the fixation device 500 includes a two-piece clamshell configuration for the frustoconical outer main body part 506 of the fixation sleeve 505, with the two halves 506' and 506" of the clamshell configuration being securable together via bolts or other securing members known to those skilled in the art (not depicted in FIGS. 9 and 10). An inner central passage 515 formed by mating the two halves 505', 505" of the clamshell of the fixation sleeve 505 is configured to receive an inner tube 507. The inner tube 507 extends past the proximal end 501 of the fixation sleeve 505 and terminates in a clamp 530 having a similar configuration as that described with reference to the exemplary embodiments of FIGS. 2-8 in terms of the structure of the C-clamp with extensions and a cam and lever to move the clamp 530 between relatively more open and closed configurations to place the fixation device 500 in the released and secured states, respectively. For simplification and ease of illustration, the lever component of the clamp 530 is not illustrated in FIGS. 9 and 10.

Bearings 509 are press fit onto the outer surface 507' of the inner tube 507 and thus captured, with the inner tube 507, by the two clamshell halves 506', 506" of the sleeve 506. The bearings 509 permit the inner tube 50 to rotate relative to the sleeve 506. Accordingly, with a cannula held by the clamp 530 and extending through the inner tube 507, the cannula can be held in a fixed axial position relative to the fixation sleeve 505, but able to rotate in either direction relative to the outer main body 506. As above, such a configuration permits the cannula to rotate during a surgical procedure without risk of transferring the rotational load to the sleeve 505 and consequently to sutures securing the fixation device 500 to a body wall at the incision site.

A variety of configurations and arrangements can be used for the bearings 509, with the number and arrangement shown being exemplary and nonlimiting. For example, exemplary embodiments of the present disclosure contemplate using needle bearings, ball bearings, thrust bearings, etc. The bearings also may have a variety of positions around the circumference and along the length of the inner tube 507 between the ends 501, 502 of the outer main body part 506. If the fixation device is otherwise configured to be reusable and autoclavable, high temperature bearings and bearing materials can be employed.

Other aspects such as material selection, the inclusion or absence of surface features on the outer surface of the conical sleeve, anti-roll features, and suture stays are not described here, but it should be understood that those elements, as have been described above with respect to other exemplary embodiments, also may be included in the exemplary embodiment of FIGS. 9 and 10.

As described above with respect to various other exemplary embodiments, the multi-component structure and ability to relatively easily disassemble the fixation device 500 into its multiple components facilitates access to various portions of the device to provide for thorough cleaning of the fixation device 500 and/or facilitates repair and replacement of component parts, for example, that may wear before others.

The present disclosure further contemplates various exemplary embodiments of a cannula fixation device wherein the clamp that secures to the cannula is configured to provide a friction fit with the cannula, thereby eliminating use of moving components that position the clamp between open and closed positions. In various exemplary embodiments relying on such a friction fit, the friction fit is sufficient to hold the cannula in a fixed axial position relative to the fixation device during a surgical procedure such that the fixation device is in a secured state. However, under a sufficient axial force on the cannula, such as by personnel desiring to uncouple the cannula from the fixation device, the friction fit can be overcome to enable the cannula to be released from the fixation device so as to place the fixation device in a released state.

Figure 12:
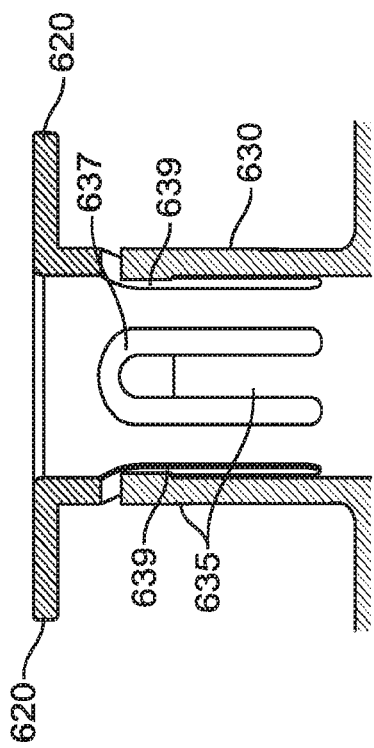
FIG. 12 is a detailed longitudinal sectional view of the clamp of the cannula fixation device of FIG. 11.
Figure 13:
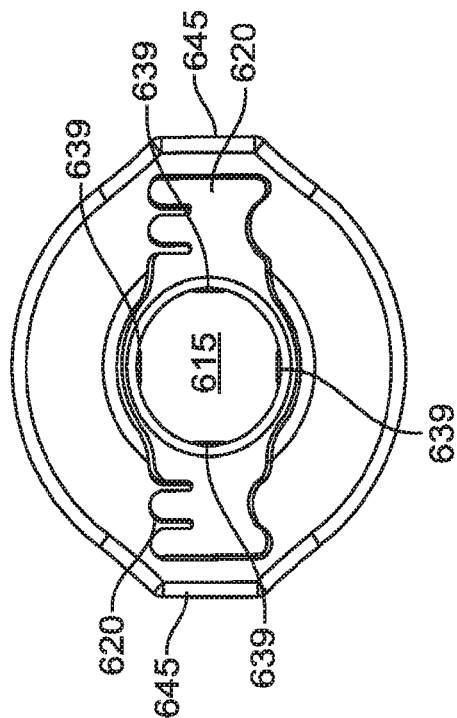
FIG. 13 is an axial end view of the cannula fixation device of FIG. 11 observed from a direction facing the clamp.
Figure 11:
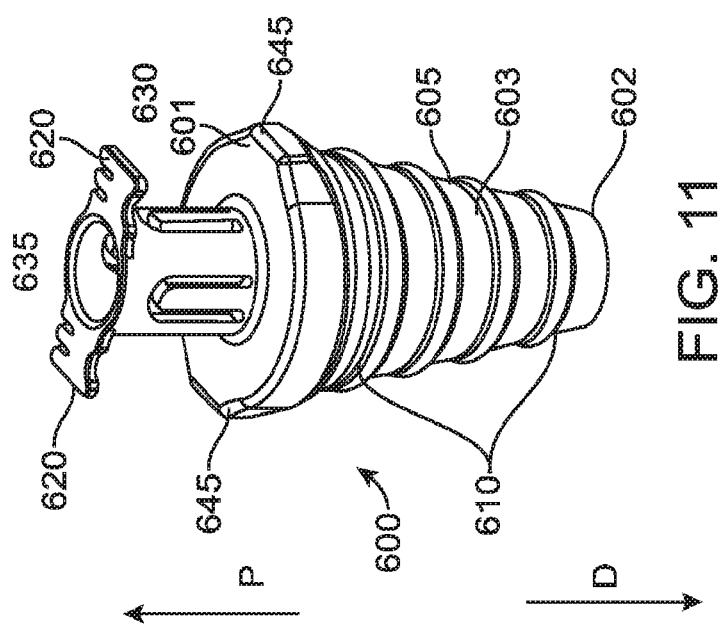
FIG. 11 is a perspective view of another exemplary embodiment of a cannula fixation device in accordance with the present disclosure.

An exemplary embodiment of a cannula fixation device that includes a clamp configured to provide a friction fit with a cannula to retain the cannula in an axial position relative to the conical fixation sleeve is depicted in FIGS. 11-13. In FIGS. 11-13, the cannula fixation device 600 includes a frusto-conical shaped fixation sleeve 605 having a configuration generally similar to the exemplary embodiments described above, including an outer (lateral) surface 603 profile that tapers from a proximal end 601 to a distal end 602 and an inner central passage 615 configured to receive a cannula (not shown) to be inserted through the fixation device 600. The outer surface 603 of the fixation device 600 is shown with ribs 610 configured to facilitate an interference fit and gripping of a body wall into which the fixation device is inserted, as described above. However, such ribs 610 are optional and other configurations and arrangements of surface features may be used in lieu of or in addition to the ribs 610, or the outer surface 603 of the fixation sleeve 605 may be smooth and lack such surface features. Further, as illustrated in FIGS. 11 and 13, the fixation device 600 can include anti-rotational bosses 645, similar to the bosses 245 described with reference to the exemplary embodiment of FIGS. 2-5. As described above, such anti-rotational features are optional and the configuration of the bosses 645 is exemplary and non-limiting only, with other arrangements, numbers, and configurations of anti-rotational features being contemplated as within the scope of the present disclosure.

Extending from the proximal end 601 of the sleeve 605 is a clamp 630 that can be integrally formed with the sleeve 605 and can form a neck of the overall fixation device 600. The clamp 630 is a generally hollow tubular member that has a passage leading to the central passage 615 and is sized to receive a cannula. Disposed around the periphery of the tube forming the clamp 630 are a plurality of spring fingers 635. As best illustrated in FIG. 12, the spring fingers 635 are defined by inverted U-shaped cutouts 637 in a side wall of the clamp 630. In the exemplary embodiment of FIGS. 11-13, four spring fingers 635 are disposed around the periphery of the tube member forming the clamp 630. The spring fingers 635 are biased radially inward. When a cannula is inserted through the clamp 630's passage and into the central passage 615, the spring fingers 635 provide a friction interference fit with the cannula in a radially inward direction (normal to the cannula outer surface) to achieve clamping to fix the axial position of the cannula. The amount of clamping force exerted by the fingers 635 on the cannula depends on the amount of deflection each finger experiences due to the cannula's insertion in the clamp 630.

Although the fingers 635 are configured to provide a clamping force in a normal direction to the outer surface of a cannula held by the clamp 630, the fingers 635 also provide a relatively low coefficient of friction with the cannula so as to permit rotation of the cannula relative to the fixation device 600. Thus, as with other exemplary embodiments described herein, the clamp 630 of the fixation device 600 permits the cannula to rotate without transferring a rotational load to the fixation sleeve 605 and thus to sutures attaching the fixation device 600 to the body wall of a patient.

In an exemplary embodiment, the tips 639 of the fingers may have a slightly radiused, convex profile such that the tips 639 engage with the cannula while the rest of the length of the fingers 635 do not engage the cannula. The clamp 630 and fingers 635 can be made of a variety of materials, such as biomedical grade materials that are sufficiently non-galling and durable, including various stainless steel alloys and flexible, durable plastics as have been described herein and as those having ordinary skill in the art would understand how to select based on the present disclosure.

The exemplary embodiment of FIGS. 11-13 also may include suture stays 620. In the exemplary embodiment of FIGS. 11-13, however, rather than positioning the suture stays so as to extend from the fixation sleeve, the suture stays 620 of the fixation device 600 extend radially outward from a proximal portion of the tube of the clamp 630. Although other positioning and arrangements of the suture stays could be used, the arrangement depicted may assist in manufacture of the fixation device 600 as a single machined piece, for example, using wire electrical discharge machining that may facilitate the formation of the cutouts 637.

As above, the fixation device 600 can be made as a single, structure, such as, for example via machining in one piece. Accordingly, the fixation device 600 can be made of a suitable, medical grade metal or metal alloy, such as, for example, stainless steel. The fixation device 600 also may be made via molding, for example, using suitable thermoplastic materials, which may be more conducive to disposable applications. The configuration of the fixation device 600 as a single piece integral structure and the generally easily accessed portions of the fixation device 600 also facilitates cleaning of the fixation device 600, allowing for reuse of the device if desired.

Other non-limiting exemplary embodiments of cannula fixation devices that are similar in design to the fixation device 600 but with differing arrangements for clamp spring fingers are illustrated in FIGS. 14-17. In the exemplary embodiment of FIGS. 14 and 15, the fixation device 700 includes a clamp 730 with spring fingers 735 (six being depicted as an exemplary and nonlimiting number and arrangement in FIGS. 14 and 15) defined by longitudinal slits or cutouts 737 being periodically made around the clamp tube. The longitudinal slits begin at the proximal end of the clamp 730 and thus the tips 739 of the fingers form the axial free end of the clamp 730, as opposed to being axially spaced from the proximal end of the clamp as in the fixation device 600.

The fixation device 800 of the exemplary embodiment of FIGS. 16 and 17 is similar to that of FIGS. 14 and 15 except that the clamp 630 includes only two larger spring fingers 835, which have a generally crescent shaped transverse cross-section. Those having ordinary skill in the art would appreciate that the number, size, and arrangement of the spring fingers in the exemplary embodiments of FIGS. 11-17 can be modified based on desired clamping forces with the cannula, desired coefficient of friction to permit relatively unhindered rotation of the cannula relative to the fixation device, manufacturability, material selection, and other similar factors.

Other features of the fixation devices 700 and 800 can be similar to those described with reference to FIGS. 11-13, and are not further described here. For example, the fixation devices 700 and 800 are shown without suture stays and without anti-rotational features, however, those having ordinary skill in the art would appreciate that the fixation devices 700 and 800 can incorporate such features and those features can have any of the configurations and arrangements as have been described herein with respect to other exemplary embodiments. Moreover, it should be appreciated that the exemplary embodiments of FIGS. 14-17 are depicted with surface features (e.g., ribs) on the outer surface 703, 803 of the fixation sleeves 705, 805, but those surface features are optional and further, arrangements and types of surface features other than ribs can be used and are considered as within the scope of the present disclosure.

Referring now to FIGS. 18-21, another exemplary embodiment of a cannula fixation device having a clamp that utilizes an interference, friction fit to hold an axial position of a cannula relative to the fixation device is shown. The fixation device 900 is provided as a two-piece structure having a fixation sleeve 905 that has a configuration similar to the fixation sleeve 205. However, the clamp 930 of the fixation device 900 is provided as an elastomeric grommet that can be stretched over the upper end of the neck 925 of the sleeve 905. The clamp 930 is provided with a tab 950 that extends radially outward from the grommet of the clamp 930 to provide a grasping surface, for example for a thumb and finger to grasp, for removal of the clamp 930 from the frusto-conical fixation sleeve 905. The inner peripheral surface profile of the grommet can provide an interlocking fit with an outer surface profile of the proximal end of the neck 925, as shown best in the longitudinal sectional view of FIG. 19, so that the grommet can be held in place once stretched over and positioned around the neck 925. The ability to relatively easily remove the clamp 930 from the sleeve 905, as shown in the views of FIGS. 20 and 21 depicting the sleeve 905 and clamp 930, respectively, can facilitate cleaning of the fixation device 900 by enabling better access to the surfaces of the device.

The grommet includes an opening 932 that receives a cannula (not shown) and is slightly smaller than the cannula outer diameter. In this way, a lip of the grommet that surrounds and defines the boundary of the opening 932 engages the outer surface of the cannula and provides a friction fit with the cannula to retain the cannula in a fixed axial position at least during a surgical procedure, in a manner similar to the spring fingers of the embodiments of FIGS. 11-17 described above. As with the spring fingers in those embodiments, the clamp 930 also permits axial rotation of the cannula relative to the fixation device and sleeve 905 by allowing the rotational frictional force between the grommet and the cannula to be overcome, including during a surgical procedure with the cannula held in an axial position. In this way, the cannula can rotate relative to both the sleeve 905 and the clamp 930, while maintaining its relative axial position with respect to both of those structures. However, if needed, surgical personnel can relatively easily remove the cannula from the fixation device by exerting a sufficient axial force to release the cannula from the fixation device 900.

In the exemplary embodiment of FIGS. 18-21, the fixation sleeve 905 can be made of various relatively non-galling and durable, biomedical grade metals and thermoplastics as have been described above with respect to other exemplary embodiments. The elastomeric clamp 930 can be made of various suitable elastomeric materials, such as, for example, silicone, polyisoprene, and/or other thermoplastic elastomers. The choice of material may depend on a variety of factors, including for example, whether the device and/or clamp 930 are intended to be reusable or disposable (e.g., single use).

As described with reference to other exemplary embodiments herein, the fixation device 900 may include suture stays, shown in FIGS. 18 and 20 as extending radially outward from the neck 925, although other configurations shown and described herein also could be employed. Further, the fixation sleeve 905 may optionally include anti-rotational features (not shown), and be either smooth or have surface features such as ribs (shown) on an outer surface of the fixation sleeve 905 to enhance gripping with the body wall.

Exemplary embodiments of cannula fixation devices described herein may be used, for example, with a da Vinci Si® Surgical System, Single Site™ da Vinci® Surgical System, or a da Vinci® Xi™ Surgical System, and other systems commercialized by Intuitive Surgical, Inc. of Sunnyvale, Calif. However, those having ordinary skill in the art will appreciate the cannula fixation devices, systems, and methods in accordance with various exemplary embodiments may be used with cannulas of other minimally invasive surgical systems, including in both manual and other teleoperated, computer-assisted cannula-based surgical systems.

Various exemplary embodiments of cannula fixation devices in accordance with the present disclosure also contemplate differing sizes of fixation devices so as to accommodate and receive different sized outer diameters of cannulas. Accordingly, the clamp openings and central passages of the fixation sleeves may vary in size to be able to clamp onto different sized cannulas. Materials for fixation devices may be chosen from a variety of biomedical grade materials, such as stainless steel, metal alloys, and various plastics. Material selection may depend on whether the fixation devices are configured for single use and thus are disposable or whether the fixation devices are configured to be reused and thus cleaned and sterilized (e.g., autoclaved) between uses.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one having ordinary skill in the art after having the benefit of the description herein. Changes may be made in the elements described herein without departing from the spirit and scope of the present disclosure and following claims.

This description's terminology is not intended to limit the scope of the present disclosure or claims. As used herein, the term clamp is used broadly and refers to various types of structures that can be used to hold or secure objects together to prevent movement or separation through the application of inward force or pressure. In exemplary embodiments, clamps may have parts that move relative to each other to move the clamp between a clamped, secured state and an unclamped, released state. In yet other exemplary embodiments, clamps contemplated by the present disclosure may instead work via a friction or interference fit that in a secured state can hold the cannula in a fixed position under forces that are not sufficient to overcome the friction or interference fit, and then be released from the cannula when a force sufficient to overcome the friction or interference fit is applied.

In the present disclosure, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

It is to be understood that the particular examples and embodiments set forth herein are nonlimiting, and modifications to structure, dimensions, materials, and methodologies may be made without departing from the scope of the present disclosure.

Other embodiments in accordance with the present disclosure will be apparent to those skilled in the art from consideration of the specification and practice of the exemplary embodiments disclosed herein. It is intended that the specification and exemplary embodiments be considered as exemplary only, and that the claims be entitled to their full breadth of scope, including equivalents.

What is claimed is:

1. A cannula fixation device for insertion at a surgical incision, the fixation device comprising:
   a sleeve comprising a proximal end portion, a distal end portion, and a passage connecting the proximal end portion and the distal end portion, the passage being configured to receive a cannula having a longitudinal axis; and
   a clamp rotatably coupled to the sleeve and moveable between an open position and a closed position;
   wherein:
   in the open position of the clamp, the clamp is configured to permit insertion of the cannula through the clamp and into the passage of the sleeve; and
   in the closed position of the clamp, the clamp is configured to rotatably couple the cannula, when received in the passage, to the sleeve such that the cannula is rotatable about the longitudinal axis while being maintained in a fixed axial position relative to the sleeve.

2. The cannula fixation device of claim 1, wherein the sleeve has a frusto-conical shape.

3. The cannula fixation device of claim 1, further comprising one or more sleeve surface features on an outer surface of the sleeve, the or each sleeve surface feature being configured to grip with layers at an incision site.

4. The cannula fixation device of claim 1, wherein the clamp comprises a C-clamp and a lever, movement of the lever moving the clamp between the open and closed positions.

5. The cannula fixation device of claim 4, wherein the lever comprises a cam surface configured to move into and out of engagement with the C-clamp to move the clamp between the open and closed positions.

6. The cannula fixation device of claim 1, wherein the clamp is rotatably coupled to the sleeve in a substantially fixed axial position relative to the sleeve.

7. The cannula fixation device of claim 6, wherein the clamp comprises a groove configured to receive a lip of the sleeve to rotatably couple the clamp to the sleeve.

8. The cannula fixation device of claim 7, wherein the lip and surfaces defining the groove are positioned to provide sufficient clearance to permit fluid to be flowed between the lip and the surfaces of the groove.

9. The cannula fixation device of claim 1, wherein the clamp is configured to be removable from the sleeve.

10. The cannula fixation device of claim 1, wherein the clamp is configured to engage with the cannula in a friction fit manner to maintain the axial position of the cannula.

11. The cannula fixation device of claim 10, wherein the clamp comprises a plurality of resilient spring fingers.

12. A cannula fixation device for insertion at a surgical incision, the fixation device comprising:
    a sleeve comprising a passage; and
    a clamp rotatably coupled to the sleeve in a fixed axial position relative to the sleeve;
    wherein the clamp is configured to grasp a cannula received in the passage of the sleeve such that the cannula remains in a fixed axial position relative to the sleeve as the cannula rotates relative to the sleeve.

13. The fixation device of claim 12, wherein:
    the sleeve comprises an outer surface and surface features on the outer surface; and
    the surface features are configured to grip a portion of a patient's body wall.

14. The fixation device of claim 12, wherein:
    the clamp comprises a groove; and
    the sleeve comprises a lip configured to be received in the groove.

15. The fixation device of claim 12, wherein:
    the clamp comprises a C-clamp and a lever; and
    movement of the lever moves the C-clamp between a closed position and an open position.

16. The fixation device of claim 15, wherein the lever comprises a cam surface configured to move into and out of engagement with the C-clamp to move the C-clamp between the open position and the closed position.

17. The fixation device of claim 12, wherein the clamp is removably coupled to the sleeve.

* * * * *

UNITED STATES PATENT AND TRADEMARK OFFICE
CERTIFICATE OF CORRECTION

PATENT NO. : 10,959,753 B2
APPLICATION NO. : 15/576872
DATED : March 30, 2021
INVENTOR(S) : William A. Burbank and Douglas S. Langley Page 1 of 1

It is certified that error appears in the above-identified patent and that said Letters Patent is hereby corrected as shown below:

On the Title Page

Item [54], replace "CANULA" with --CANNULA--.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*